(12) United States Patent
Rashid et al.

(10) Patent No.: US 8,518,438 B2
(45) Date of Patent: Aug. 27, 2013

(54) HIGHLY CONCENTRATED LIQUID ACETAMINOPHEN SOLUTIONS

(75) Inventors: Abdul Rashid, Livingston, NJ (US); Minh Tran, Secaucus, NJ (US)

(73) Assignee: Enspire Group, LLC, South Plainfield, NJ (US)

( * ) Notice: Subject to any disclaimer, the term of this patent is extended or adjusted under 35 U.S.C. 154(b) by 0 days.

(21) Appl. No.: 13/327,148

(22) Filed: Dec. 15, 2011

(65) Prior Publication Data

US 2012/0183608 A1 Jul. 19, 2012

Related U.S. Application Data

(60) Provisional application No. 61/433,087, filed on Jan. 14, 2011.

(51) Int. Cl.
*A61K 9/48* (2006.01)

(52) U.S. Cl.
USPC ............ 424/455; 424/451; 424/452; 424/456

(58) Field of Classification Search
USPC .................................. 424/451–463
See application file for complete search history.

(56) References Cited

U.S. PATENT DOCUMENTS

| | | |
|---|---|---|
| 5,071,643 A | 12/1991 | Yu et al. |
| 5,141,961 A | 8/1992 | Coapman |
| 5,154,926 A | 10/1992 | Kawasaki et al. |
| 5,409,907 A | 4/1995 | Blase et al. |
| 5,505,961 A | 4/1996 | Shelley et al. |
| 5,510,389 A * | 4/1996 | Dhabhar ................ 514/629 |
| 5,641,512 A | 6/1997 | Cimiluca |
| 6,160,020 A | 12/2000 | Ohannesian et al. |
| 6,783,731 B1 | 8/2004 | Arter et al. |
| 7,029,698 B2 | 4/2006 | Waranis et al. |
| 2003/0096872 A1 | 5/2003 | Waranis et al. |

FOREIGN PATENT DOCUMENTS

| | | |
|---|---|---|
| WO | 03/013481 | 2/2003 |
| WO | WO 03013481 A1 * | 2/2003 |
| WO | WO 2009/066146 | 5/2009 |

OTHER PUBLICATIONS

*International Search Report*, PCT Application No. PCT/US2012/020750, mailed Aug. 14, 2012 (3 pages).

* cited by examiner

*Primary Examiner* — Michael G Hartley
*Assistant Examiner* — Micah-Paul Young
(74) *Attorney, Agent, or Firm* — Fox Rothschild LLP

(57) ABSTRACT

Liquid softgel fill formulations include (i) 26-32% by weight acetaminophen, (ii) 47-51% by weight polyethylene glycol having an average molecular weight of 200-800, (iii) 3-7% by weight propylene glycol, (iv) 9-13% by weight Povidone K17, and (v) 6-10% by weight purified water. The fill formulations are free of alkali metal ions. Also disclosed are a method of preparing the above-described fill formulations and softgel capsules containing the same fill formulations.

20 Claims, No Drawings

HIGHLY CONCENTRATED LIQUID ACETAMINOPHEN SOLUTIONS

CROSS-REFERENCE TO RELATED APPLICATION

This application claims the benefits of the priority pursuant to 35 U.S.C. §119(e) of U.S. Provisional Patent Application No. 61/433,087, filed Jan. 14, 2011. The content of the prior application is incorporated herein by its entirety.

BACKGROUND

Acetaminophen is an over-the-counter drug commonly used to relieve headaches and to reduce fever.

A highly concentrated solution of acetaminophen allows a high dose of acetaminophen (e.g., 325 mg) to be encapsulated in a small softgel capsule for easy swallowing. It also enhances the bioavailability of acetaminophen. However, acetaminophen tends to recrystallize in such a solution.

There is a need to develop a new method for preparing highly concentrated acetaminophen solutions suitable for encapsulation in softgel capsules.

SUMMARY

In one aspect, this invention features a liquid softgel fill formulation containing acetaminophen as the only active ingredient. The liquid softgel fill formulation includes (i) acetaminophen, 26-32% by weight (e.g., 28-30%); (ii) polyethylene glycol having an average molecular weight of 200-800 (e.g., 300-500), 47-51% by weight (e.g., 50%); (iii) propylene glycol, 3-7% by weight (e.g., 5%); (iv) Povidone K17, 9-13% by weight (e.g., 10%); and (v) purified water, 6-10% by weight (e.g., 7%). The formulation is free of alkali metal ions.

In one embodiment of the above-described liquid softgel fill formulation, the acetaminophen is 28% by weight, the polyethylene glycol is 50% by weight and has an average molecular weight of 400, the propylene glycol is 5% by weight, the Povidone K17 is 10% by weight and the water is 7% by weight.

In another aspect, this invention features a method of preparing a liquid softgel fill formulation, containing acetaminophen and, optionally, one or more other active ingredients. The method includes following steps: (a) stirring polyethylene glycol and propylene glycol to obtain a mixture, the polyethylene glycol having an average molecular weight of 200-800 (e.g., 300-500), (b) heating the mixture to a temperature of 170±10° F. (e.g. 170±5° F.) with stirring to obtain a heated mixture, (c) adding Povidone K17 to the heated mixture with stirring at the same temperature to obtain a clear solution, (d) adding purified water to the clear solution with stirring at the same temperature to obtain an aqueous solution, (e) adding acetaminophen to the aqueous solution with stirring at the same temperature to obtain an acetaminophen solution, (f) stirring the acetaminophen solution at the same temperature for at least 30 minutes (e.g., 45 minutes) to obtain a clear acetaminophen solution, and (g) cooling to ambient temperature and deaerating the clear acetaminophen solution.

In still another aspect, this invention features a softgel capsule containing acetaminophen as the only active ingredient. It includes (i) a soft gelatin shell, and (ii) the above-described liquid softgel fill formulation within the shell.

Preferably, the total amount of the acetaminophen in the softgel capsule is 325-360 mg (e.g., 325 mg).

The details of one or more embodiments of the invention are set forth in the description below. Other features, objects, and advantages of the invention will be apparent from the description of examples and also from the appending claims.

DETAILED DESCRIPTION

This invention is based on the discovery that highly concentrated acetaminophen solutions can be used as liquid softgel fill formulations without recrystallization for an extended period of time (e.g., eight months). These formulations, when encapsulated into softgel capsules, provide long term stability and acceptable dosage to consumers. In this connection, they can be used to manufacture softgels containing 325 mg acetaminophen as a clear solution.

The liquid softgel fill formulation of this invention includes (i) acetaminophen; (ii) polyethylene glycol having an average molecular weight of 200-800; (iii) propylene glycol; (iv) Povidone K17; and (v) purified water. The formulation is free of alkali metal ions, i.e., lithium, sodium, potassium, rubidium, and caesium cations.

Polyethylene glycol, also known as "PEG," has a general formula of $H(OCH_2CH_2)_nOH$, where n is greater than or equal to 4. It is designated by its average molecular weight. For example, polyethylene glycol 400 (PEG-400) has an average molecular weight of about 400. See Cosmetic Ingredient Dictionary, Third Edition (1982), pages 201-203; and The Merck Index, Tenth Edition, entry 7441, page 1092 (1983). Polyethylene glycol used in this invention, having an average molecular weight of 200-800, is a clear viscous liquid or a white solid at room temperature, and can be dissolved in water and many organic solvents. PEG 400 is especially preferred.

Propylene glycol is an organic compound having a formula $HOCH_2CHOHCH_3$. A clear viscous liquid, it is miscible with water, acetone, and chloroform.

The term "Povidone" refers to polyvinylpyrrolidone, a water-soluble polymer. The term "K17" refers to a K value defined by Fikentscher. The K value is an index for correlating relative viscosity with the average degree of polymerization. See Cellulose Chem. 1932, 13, 60. The K value of Povidone is calculated by the following formula:

$$K = (1.5 \log \eta_{rel} - 1)/(0.15 + 0.003c) + (300c \log \eta_{rel} + (c + 1.5c \log \eta_{rel})^2)^{1/2}/(0.15c + 0.003c^2)$$

$\eta_{rel}$: Relative viscosity of aqueous Povidone solution to water. c: Content of Povidone in an aqueous Povidone solution (w/w %).

Note that, in the liquid softgel formulation of this invention, polyethylene glycol having an average molecular weight of 200-800, propylene glycol, and Povidone K17 are all used to increase solubility of acetaminophen.

Below is an exemplary procedure for preparing a liquid softgel fill formulation of this invention.

PEG-400 and propylene glycol are mixed with stirring at high speed (e.g., 250-350 revolutions per minute). The mixture is slowly heated to 170±10° F. Povidone K17 is then added to the mixture at the same temperature. After the mixture turns into a clear solution with constant stirring, purified water is added, followed by addition of acetaminophen. The acetaminophen-containing solution is further stirred at 170±10° F. for 30 minutes until it becomes clear. The clear acetaminophen solution is then removed from the heat source and deaerated in a vacuum desiccator (a vacuum between 26 to 30 inches of mercury) at room temperature for 20-30 minutes.

The liquid softgel fill formulation thus obtained can be screened by visual detection periodically (e.g., monthly) so as to determine whether there is any crystal formed therein. The acetaminophen contained in the fill formulation can be confirmed and quantified by thin layer chromatography and high performance liquid chromatography. Microbial limits tests can be performed to determine the numbers of aerobic organisms, yeasts, and molds in the fill formulation.

The liquid softgel fill formulation can be encapsulated in soft gelatin shells to form softgel capsules using a conventional rotary die process. Suitable soft gelatin shells may include (i) gelatin, 35-60% by weight; (ii) glycerin, 10-15% by weight; (iii) sorbitol, 11-20% by weight; (iv) purified water, 20-40% by weight; and (v) artificial color, 0.0001-0.002% by weight.

The softgel capsules of the invention can also be prepared by other methods well known in the art. See e.g., P. K. Wilkinson et al., "Softgels: Manufacturing Considerations," Drugs and the Pharmaceutical Sciences, 41 (Specialized Drug Delivery Systems); P. Tyle, Ed. (Marcel Dekker, Inc., New York, 1990) 409-449; F. S. Hom et al., "Capsules, Soft" Encyclopedia of Pharmaceutical Technology, vol. 2; J. Swarbrick and J. C. Boylan, eds. (Marcel Dekker, Inc., New York, 1990) pp. 269-284; M. S. Patel et al., "Advances in Softgel Formulation Technology," Manufacturing Chemist, vol. 60, no. 7, pp. 26-28 (July 1989); M. S. Patel et al., "Softgel Technology," Manufacturing Chemist, vol. 60, no. 8, pp. 47-49 (August 1989); R. F. Emerson, "Softgel (Soft Gelatin Capsule) Update," Drug Development and Industrial Pharmacy (Interphex '86 Conference), vol. 12, no. 8 & 9, pp. 1133-1144 (1986); and W. R. Ebert, "Soft Elastic Gelatin Capsules: A Unique Dosage Form," Pharmaceutical Technology, vol. 1, no. 5, pp. 44-50 (1977).

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Preparation of a Highly Concentrated Acetaminophen Formulation

Polyethylene glycol 400 (575 mg) and propylene glycol (54.5 mg) were mixed with stirring at high speed (250-350 rpm). The mixture was slowly heated to 170±5° F. Povidone K17 (115.0 mg) was then added to the mixture at the same temperature. After the mixture turned into a clear solution with constant stirring, purified water (80.5 mg) was added, followed by acetaminophen (325 mg, manufactured by Mallinkrodt). The acetaminophen-containing solution was further stirred at 170±5° F. for 45 minutes until it became clear. The clear acetaminophen solution was then removed from the heat source and deaerated in a vacuum desiccator (a vacuum between 26 to 30 inches of mercury) at room temperature for 20-30 minutes. The solution was then visually evaluated. It remained clear for more than eight months.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A liquid softgel fill formulation containing acetaminophen as the only active ingredient, which formulation comprises:
   26-32% by weight acetaminophen,
   47-51% by weight polyethylene glycol having an average molecular weight of 200-800,
   3-7% by weight propylene glycol,
   9-13% by weight polyvinylpyrrolidone with a K value of 17, and
   6-10% by weight purified water, wherein the formulation is free of alkali metal ions, wherein the formulation remains clear for eight months at room temperature.

2. The liquid softgel fill formulation of claim 1, wherein the acetaminophen is 28-30% by weight.

3. The liquid softgel fill formulation of claim 1, wherein the acetaminophen is 28% by weight.

4. The liquid softgel fill formulation of claim 1, wherein the polyethylene glycol has an average molecular weight of 300-500.

5. The liquid softgel fill formulation of claim 4, wherein the polyethylene glycol has an average molecular weight of 400.

6. The liquid softgel fill formulation of claim 1, wherein the acetaminophen is 28% by weight, the polyethylene glycol is 50% by weight and has an average molecular weight of 400, the propylene glycol is 5% by weight, the polyvinylpyrrolidone with a K value of 17 is 10% by weight, and the water is 7% by weight.

7. A method of preparing a liquid softgel fill formulation of claim 1, which method comprises:
   (a) stirring polyethylene glycol and propylene glycol to obtain a mixture, the polyethylene glycol having an average molecular weight of 200-800,
   (b) heating the mixture to a temperature of 170±10° F. with stirring to obtain a heated mixture,
   (c) adding polyvinylpyrrolidone with a K value of 17 to the heated mixture with stirring at the same temperature to obtain a clear solution,
   (d) adding purified water to the clear solution with stirring at the same temperature to obtain an aqueous solution,
   (e) adding acetaminophen to the aqueous solution with stirring at the same temperature to obtain an acetaminophen solution,
   (f) stirring the acetaminophen solution at the same temperature for at least 30 minutes to obtain a clear acetaminophen solution, and
   (g) cooling to ambient temperature and deaerating the clear acetaminophen solution.

8. The method of claim 7, wherein the polyethylene glycol has an average molecular weight of 300-500.

9. The method of claim 7, wherein the temperature is in a range of 170±5° F.

10. The method of claim 7, wherein the acetaminophen solution in step (f) is stirred for at least 45 minutes.

11. The method of claim 7, wherein the polyethylene glycol has an average molecular weight of 400, the temperature is 170±5° F. and the acetaminophen solution is stirred for at least 45 minutes.

12. A softgel capsule containing acetaminophen as the only active ingredient, which softgel capsule comprises:
- a soft gelatin shell, and
- a liquid softgel fill formulation within the shell, the liquid softgel fill formulation including:
- 26-32% by weight acetaminophen,
- 47-51% by weight polyethylene glycol having an average molecular weight of 200-800,
- 3-7% by weight propylene glycol,
- 9-13% by weight polyvinylpyrrolidone with a K value of 17, and
- 6-10% by weight purified water, wherein the formulation is free of alkali metal ions, wherein the formulation remains clear for eight months at room temperature.

13. The softgel capsule of claim 12, wherein the acetaminophen is 28-30% by weight.

14. The softgel capsule of claim 12, wherein the acetaminophen is 28% by weight.

15. The softgel capsule of claim 12, wherein the polyethylene glycol has an average molecular weight of 300-500.

16. The softgel capsule of claim 15, wherein the polyethylene glycol has an average molecular weight of 400.

17. The softgel capsule of claim 12, wherein the acetaminophen is 28% by weight, the polyethylene glycol is 50% by weight and has an average molecular weight of 400, the propylene glycol is 5% by weight, the polyvinylpyrrolidone with a K value of 17 is 10% by weight, and the water is 7% by weight.

18. The softgel capsule of claim 12, wherein the total amount of the acetaminophen is 325-360 mg.

19. The softgel capsule of claim 18, wherein the total amount of the acetaminophen is 325 mg.

20. The softgel capsule of claim 17, wherein the total amount of the acetaminophen is 325-360 mg.

* * * * *